United States Patent [19]

Archer

[11] 4,105,659

[45] Aug. 8, 1978

[54] 1,2,3,4,5,6-HEXAHYDRO-2,6-METHANO-3-BENZAZOCINES

[75] Inventor: Sydney Archer, Bethlehem, N.Y.

[73] Assignee: Sterling Drug Inc., New York, N.Y.

[21] Appl. No.: 342,768

[22] Filed: Feb. 5, 1964

Related U.S. Application Data

[63] Continuation-in-part of Ser. No. 72,844, Dec. 1, 1960, abandoned, Ser. No. 239,777, Nov. 23, 1962, Pat. No. 3,372,165 and Ser. No. 251,721, Jan. 16, 1963, Pat. No. 3,250,678.

[51] Int. Cl.$^2$ .............................................. C07D 221/26
[52] U.S. Cl. ................................. 260/293.54; 424/267; 424/DIG. 13
[58] Field of Search ................................... 260/293.54

[56] References Cited

U.S. PATENT DOCUMENTS

| | | | |
|---|---|---|---|
| 3,250,678 | 5/1966 | Archer | 260/293.54 X |
| 3,723,440 | 3/1973 | Freter et al. | 260/293.54 |

FOREIGN PATENT DOCUMENTS

| | | | |
|---|---|---|---|
| 611,000 | 5/1962 | Belgium | 260/293.54 |

*Primary Examiner*—John D. Randolph
*Attorney, Agent, or Firm*—B. Woodrow Wyatt

[57] ABSTRACT

1,2,3,4,5,6-Hexahydro-3-lower alkenyl-6-($R^1$)-11-($R^2$)-8-hydroxy-2,6-methano-3-benzazocines, wherein $R^1$ and $R^2$ are hydrogen or lower alkyl, and certain ethers and esters thereof, are obtained from analogous 3-unsubstituted compounds. The products have pharmacodynamic activity and are useful as antagonists of strong analgesic agents, such as morphine and meperidine, and are useful in humans as agents for producing analgesia.

9 Claims, No Drawings

1,2,3,4,5,6-HEXAHYDRO-2,6-METHANO-3-BENZAZOCINES

This application is a continuation-in-part of my prior copending applications: Ser. No. 72,844, filed Dec. 1, 1960, now abandoned; Ser. No. 239,777, filed Nov. 23, 1962, now U.S. Pat. No. 3,372,165, issued Mar. 5, 1968; and Ser. No. 251,721, filed Jan. 16, 1963, now U.S. Pat. No. 3,250,678 issued May 10, 1966.

This invention relates to derivatives of 1,2,3,4,5,6-hexahydro-2,6-methano-3-benzazocine.

The novel compounds of this invention defined by structural formulas I and II hereinbelow have pharmacodynamic activity and are useful as antagonists of certain strong analgesic agents, such as morphine and meperidine, and are useful in humans as agents for producing analgesia, thus relieving pain.

My new compounds are, in one group, the 1,2,3,4,5,6-hexahydro-3-(Z)-6-($R^1$)-11-($R^2$)-8-($R^3$-O-)2,6-methano-3-benzazocines having the structural formula

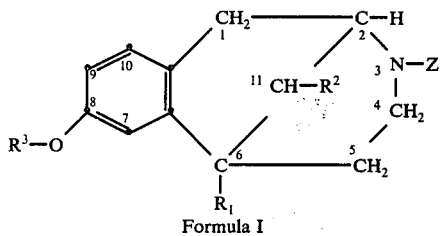

Formula I and, in another group, the 1,2,3,4,5,6-hexahydro-3-(Y)-6,11-dimethyl-8-($R^3$-O-)-2,6-methano-3-benzazocines having the structural formula

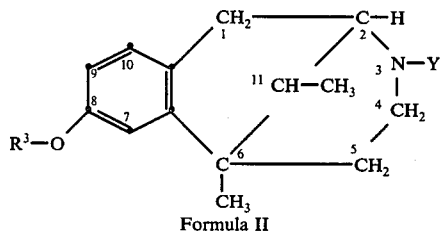

Formula II

In each of Formulas I and II, $R^3$ is a member of the group consisting of hydrogen, lower alkenyl, lower alkanoyl, cycloalkanecarbonyl, and pyridinecarbonyl. When $R^3$ is lower alkenyl, it preferably contains 3–6 carbon atoms, including for example allyl, methallyl, 3,3-dimethylallyl, and the like. When $R^3$ is lower alkanoyl, it preferably contains 1–6 carbon atoms, including for example formyl, acetyl, propionyl, butyroyl, isobutyroyl, and caproyl. When $R^3$ is cycloalkanecarbonyl, it preferably contains 4–7 carbon atoms, including for example cyclopropanecarbonyl, cyclobutanecarbonyl, cyclopentanecarbonyl, and cyclohexanecarbonyl. When $R^3$ is pyridinecarbonyl, it includes 2-pyridinecarbonyl or picolinoyl, 3-pyridinecarbonyl or nicotinoyl, and 4-pyridinecarbonyl or isonicotinoyl.

In Formula I, $R^1$ is a member of the group consisting of hydrogen, methyl, ethyl, and propyl and $R^2$ is a member of the group consisting of hydrogen and methyl; and Z is lower alkenyl containing 3-6 carbon atoms. The lower alkenyl group Z includes the monovalent lower molecular weight unsaturated aliphatic hydrocarbon radicals containing at least one double bond, and having 3–6 carbon atoms, for example $-CH_2-CH=CH_2$, $-CH_2-CH=CH-CH_3$, $-CH_2CH_2CH_2-CH=CH_2$, $-CH_2-CH=C(CH_3)_2$, $-CH_2-CH=CH-CH_2CH_2CH_3$, $-CH_2CH_2-CH=CH-CH_2CH_3$, $-CH_2-C(CH_3)=CH_2$, $-CH(CH_3)-CH=CH_2$, $-CH(CH_3)-CH=C(CH_3)_2$, $-CH_2-CH=CH-CH=CH_2$, $-CH_2-CH=C=CH_2$, and the like.

In Formula II, Y is lower alkenyl containing 4–6 carbon atoms. The group Y includes the monovalent lower molecular weight unsaturated aliphatic hydrocarbon radicals containing at least one double bond and having 4–6 carbon atoms, for example $-CH_2-CH=CH-CH_3$, $-CH_2CH_2CH_2-CH=CH_2$, $-CH_2-CH=C(CH_3)_2$, $-CH_2CH_2-CH=CH-CH_2CH_3$, $-CH_2-C(CH_3)=CH_2$, $-CH(CH_3)-CH=CH_2$, $-CH(CH_3)-CH=C(CH_3)_2$, $-CH_2-CH=CH-CH=CH_2$, $-CH_2-CH=C=CH_2$, and the like.

Due to the presence of a basic tertiary amino grouping, the compounds of Formulas I and II react with organic and inorganic acids to form acid-addition salts, and, due to the presence of both a basic tertiary amino grouping and an acidic phenolic grouping, the new 1,2,3,4,5,6-hexahydro-3-(Z)-6-($R^1$)-11-($R^2$)-8-hydroxy-2,6-methano-3-benzazocines of Formula I and the new 1,2,3,4,5,6-hexahydro-3-(Y)-6,11-dimethyl-8-hydroxy-2,6-methano-3-benzozocines of Formula II have amphoteric properties; and therefore for a given compound, the particular molecular species which will predominate will depend on the pH of the environment. Thus, in strongly acidic media, the amino nitrogen will be protonated, and the predominant molecular species will be an acid-addition salt. On the other hand, in strongly alkaline media, the predominant molecular species of the 8-hydroxy compounds, i.e., when $R^3$ is hydrogen, will be that of a phenolate ion; and under pH conditions intermediate between these extremes, the proportion of the undissociated molecular species will increase to reach a maximum as the isoelectric point is approached, the form which is isolable at the isoelectric point being conveniently termed the isoelectric form.

My new compounds can exist in stereochemically isomeric forms, that is, optical isomers and geometric isomers. If desired, the isolation or the production of a particular stereochemical form can be accomplished by application of the general principles known in the prior art.

The acid-addition salt forms and the phenoxide forms of my new compounds are useful not only as antagonists of certain strong analgesic agents and as analgesic agents, as above-indicated, but are also useful for characterizing and identifying purposes, and in isolation or purification procedures. Moreover, the acid-addition salts and the phenoxides are sources of the free base forms and the isoelectric forms, by reaction with bases or acids, respectively, and accordingly all of the acid-addition salts and the phenoxides, regardless of considerations of solubility, toxicity, physical form, or the like of a particular compound are useful for the purposes of my invention.

It will be appreciated from the above that if one or more of the characteristics, such as solubility, molecular weight, physical appearance, toxicity, or the like of a given free base, isoelectric, phenoxide, or acid-addition salt form of a particular compound render that form unsuitable for the purpose at hand, it can be readily converted to another, more suitable form.

The new compounds of my invention wherein $R^3$ in Formulas I and II is hydrogen can be conveniently prepared in their isoelectric forms by N-alkylating the respective corresponding secondary amines. Thus, the 8-hydroxy compounds of Formula I are obtained by heating a 1,2,3,4,5,6-hexahydro-6-($R^1$)-11-($R^2$)-8-hydroxy-2,6-methano-3-benzazocine with an alkylating agent having the structural formula Z-An, and the 8-hydroxy compounds of Formula II are obtained by heating a 1,2,3,4,5,6-hexahydro-3-(Y)-6,11-dimethyl-8-hydroxy-2,6-methano-3-benzozocine with an alkylating agent having the formula Y-An, where Z and Y have the same meanings indicated hereinabove and An in each instance is the anion of a strong organic or inorganic acid, for instance a reactive halide or an arylsulfonate, e.g., a tosylate. These alkylations are carried out in the presence of an acid-absorbing medium, for instance an alkali metal carbonate or bicarbonate, for instance sodium bicarbonate, and preferably a suitable reaction medium is used, such as a lower alkanol, for instance methanol or ethanol, or an N,N-(di-lower alkyl)-lower alkanamide, for instance N,N-dimethylformamide or N,N-dimethylacetamide.

The new compounds of Formulas I and II bearings an ether or ester grouping at the 8-position, i.e., $R^3$ is other than hydrogen, are conveniently obtained by appropriate etherification and esterification, respectively, of the respective corresponding 8-hydroxy compounds, using any of the conventional prior art methods suitable for the etherification and esterification of phenols. Treatment of the 8-hydroxy compounds of Formulas I and II with normal or mixed acid anhydrides or the acid chloride of a lower alkanoic acid, a cycloalkanecarboxylic acid, or a pyridinecarboxylic acid yields the corresponding 8-(lower alkanoyloxy), 8-(cycloalkanecarbonyloxy), or 8-(pyridinecarbonyloxy) compounds of Formulas I and II.

The following is another though less satisfactory, method suitable for preparing the 8-hydroxy and 8-ether compounds of Formulas I and II wherein the carbon atom of Z linked to the nitrogen atom in Formula I, or the carbon atom of Y linked to the nitrogen atom in Formula II, is unbranched, so that a —CH$_2$— group in Z or Y, as the case may be, is adjacent to the nitrogen atom. A 1,2,3,4,5,6-hexahydro-6-($R^1$)-11-($R^2$)-8-hydroxy or ether-2,6-methano-3-benzazocine or a 1,2,3,4,5,6-hexahydro-6,11-dimethyl-8-hydroxy or ether-2,6-methano-3-benzazocine is acylated by treatment with one or two molecular equivalents of an acid halide or acid anhydride of an acid having the formula Z'—COOH in preparing the Formula I series and Y'—COOH in preparing the Formula II series, Z' being lower alkenyl containing 2–5 carbon atoms and Y' being lower alkenyl containing 3–5 carbon atoms. The resulting amide or ester-amide derivative is a 1,2,3,4,5,6-hexahydro-3-(Z'-CO-)-6-($R^1$)-11-($R^2$)-8-hydroxy or ether-2,6-methano-3-benzazocine having the structural formula

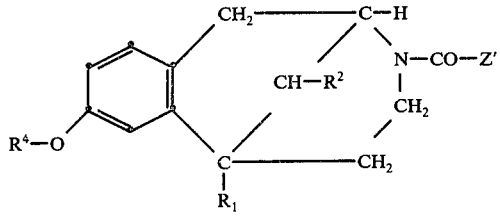

Formula III or is a 1,2,3,4,5,6-hexahydro-3-(Y'—CO—)-6,11-dimethyl-8-hydroxy or ether-2,6-methano-3-benzazocine having the structural formula

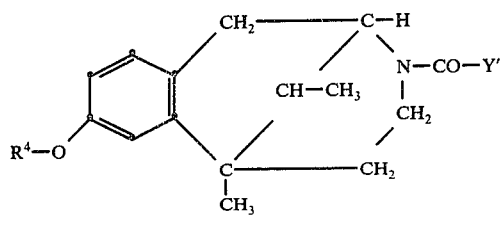

Formula IV $R^1$, $R^2$, Z', and Y' in Formulas III and IV have the same meanings hereinbefore indicated. When one molecular equivalent of the acylating agent is used, $R^4$ in each of Formulas III and IV is a member of the group consisting of hydrogen, and lower alkenyl; and $R^4$ is Z'—CO— in Formula III and is Y'—CO— in Formula IV when an 8-hydroxy starting material is acylated with two molecular equivalents of the acylating agent. Treatment of the compound of Formula III with a reducing agent such as lithium aluminum hydride effective to reduce the carbonyl of the amide group to —CH$_2$— (undesirably, to some extent ethylenic linkages are sometimes also effected) produces the 8-hydroxy or ether compound of Formulas I and II. In the N-acylation of the 8-hydroxy compounds of Formulas III and IV, in some instances both N- and O-acylation may occur to yield a mixture of the 3-acyl and 3-acyl-8-acyloxy compounds, but this is of no consequence in the over-all process, because in the reduction step both the amides and the ester-amides of Formulas III and IV when $R^4$ is either hydrogen or acyl are converted to the 1,2,3,4,5,6-hexahydro-3-(Z'—CH$_2$—)-6-($R^1$)-11-($R^2$)-8-hydroxy-2,6-methano-3-benzazocine and the 1,2,3,4,5,6-hexahydro-3-(Y'—CH$_2$—)-6,11-dimethyl-8-hydroxy-2,6-methano-3-benzazocines, respectively.

The acid-addition salt forms of my compounds are prepared from any organic acid, inorganic acid (including organic acids having an inorganic group therein), or organo-metallic acid as exemplified by organic mono- and poly-carboxylic acids such as found, for example, in Beilstein's Organische Chemie, 4th Ed., Volumes III, IV, IX, X, XIV, XVII, XIX, XXI, XXII, and XXV; organic mono- and polysulfonic acid-sulfinic acids such as found, for example in Beilstein Volumes VI, XI, XVI, and XXII; organic phoshonic and phosphinic acids such as found, for example in Beilstein Volumes XI and XVI; organic acids or arsenic and antimony such as found, for example, in Beilstein Volume XVI; organic heterocyclic carboxylic, sulfonic, and sulfinic acids such as found, for example in Beilstein Volumes XVIII, XXII, and XXV; acidic ion-exchange resins; and inorganic acids of any acid forming element or combination of elements such as found in Mellor, Comprehensive Treatise on Inorganic and Theoretical Chemistry, Longman's, Green and Co., New York, N.Y. Volumes I–XVI. In addition, other salt-forming compounds which are acidic in their chemical properties but which are not generally considered as acids in the same sense as carboxylic or sulfonic acids are also considered to be among the numerous acids which can be used to prepare the acid-addition salt forms of the compounds of this invention. Thus there are also included acidic phenolic compounds such as found, for example, in Volume VI of Beilstein, acidic compounds having "activated" or acidic hydrogen atoms, as for example, picrolonic acid, or barbituric acid derivatives having an acidic proton such as found, for example in Cox et al. Medicinal Chemistry, Vol. IV, John Wiley and Sons, Inc., New York, N.Y. (1959). Also included as salt forming agents are so-called Lewis acids which lack a pair of electrons in the outer "electron shell" and react with basic compounds having an unshared pair of electrons to form salts, for example boron trifluoride.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like. The acid-addition salts with lactic acid and with ethanesulfonic acid, for example, are water-soluble and are especially suitable forms for using my new compounds as therapeutic agents.

The acid-addition salts are prepared in conventional fashion, for instance either by direct mixing of the acid and the free base or isoelectric form or, when this is not appropriate, by dissolving either or both of the acid and the free base or isoelectric form separately in water or an organic solvent and mixing the two solutions, or by dissolving both the acid and the free base or isoelectric form together in a solvent. The resulting acid-addition salt is isolated by filtration, if it is insoluble in the reaction medium, or by evaporation of the reaction medium to leave the acid-addition salt as a residue. The acid moieties or anions in these salt forms in themselves neither novel nor critical and therefore can be any acid anion or acid-like substance capable of salt formation with the free base or isoelectric forms of my compounds.

The phenolate form of my new 8-hydroxy compounds of Formulas I and II is readily obtained for example by treating the isoelectric form with a strong alkali, such as sodium hydroxide. The alkali metal phenolates are water-soluble.

The 1,2,3,4,5,6-hexahydro-6,11-dimethyl-8-hydroxy-2,6-methano-3-benzazocine, in its racemic and optionally active cis and trans forms, used as a starting material in preparing the compounds of Formula II is known. The 1,2,3,4,5,6-hexahydro-6-($R^1$)-11-($R^2$)-8-hydroxy-2,6-methano-3-benzazocine starting materials, racemic and optically active cis and trans forms, for the preparation of the compounds of Formula I can be obtained by application of known procedures. Thus, a 3-($R^2$)-4-($R^1$)-pyridine methiodide is interacted with p-methoxybenzylmagnesium chloride; the resulting N-methyl-2-(p-methoxybenzyl)-3-($R^1$)-4-($R^2$)-1,2-dihydropyridine is reduced with sodium borohydride or by catalytic hydrogenation to produce an N-methyl-2-(p-methoxybenzyl)-3-($R^2$)-4-($R^1$)-1,2,5,6-tetrahydropyridine; and this latter product is heated with an appropriate cyclizing agent, such as concentrated hydrobromic or phosphoric acid to yield a mixture of the racemic cis (also termed the α or "normal" series) and the racemic trans (also termed the β or "iso" series) 1,2,3,4,5,6-hexahydro-3-methyl-6-($R^1$)-11-($R^2$)-8-hydroxy-2,6-methano-3-benzazocine. The reaction produces predominantly the racemic cis form, which is less soluble than the racemic trans in the reaction mixture, and thus the product which separates from the reaction mixture is further enriched with the racemic cis form. The racemic trans form can be isolated from the mother liquors. In the subsequent reaction steps, there can be used either the pure racemic cis form, the pure racemic trans form, or mixtures of the two, as desired. By acetylating the 8-hydroxyl group in the cyclization product by treatment with acetic anhydride and treatment of the resulting 8-acetoxy compound with cyanogen bromide, there is produced a 1,2,3,4,5,6-hexahydro-3-cyano-6-($R^1$)-11-($R^2$)-8-acetoxy-2,6-methano-3-benzazocine which, by heating with dilute hydrochloric acid, is converted to the desired 1,2,3,4,5,6-hexahydro-6-($R^1$)-11-($R^2$)-8-hydroxy-2,6-methano-3-benzazocine. This series of reactions is illustrated in part D of Example 1 hereinbelow.

The alkylating agents Z-An and Y-An used in the alkylation procedures for preparing my compounds are likewise readily obtainable by known methods; for instance, in one method the corresponding alcohol having the formula Z—OH or Y—OH is esterified with a strong organic or inorganic acid having the formula H-An.

By alternative system of nomenclature, the compounds of this invention are designated as benzomorphan derivatives; thus, the compounds of Formula I can be named as 2-(Z)-2'-($R^3$—O—)-5-($R^1$)-9-($R^2$)-6,7-benzomorphans, and the compounds of Formula II can be named as 2-(Y)-2'-($R^3$—O—)-5,9-dimethyl-6,7-benzomorphans.

The structures of the compounds of this invention followed from the methods of synthesis which were used and from the elementary analyses of the products obtained.

My invention is illustrated by the following examples without, however, being limited thereto.

EXAMPLE 1

1,2,3,4,5,6-Hexahydro-3-allyl-6-ethyl-11-methyl-8-hydroxy-2,6-methano-3-benzazocine A. A mixture of 2.62 g. of racemic cis 1,2,3,4,5,6-hexahydro-6-ethyl-11-methyl-8-hydroxy-2,6-methano-3-benzazocine, 1.37 g. of allyl bromide, 40 ml. of methanol, and 1.32 g. of sodium bicarbonate was stirred and refluxed for approximately six hours. The reaction mixture was then filtered to remove a small amount of solid. The filtrate was concentrated under reduced pressure and then extracted with chloroform. The chloroform extract was filtered and the filtrate was concentrated to yield a syrupy residue. This syrup solidified when triturated with diethyl ether, and the solid was collected on a filter. The solid thus obtained weighed 2.4 g. and melted at 150°–157° C. This product was dissolved in acetone and the resulting solution was filtered to remove a small amount of amorphous solid. The filtrate was concentrated and then chilled, and the solid which separated from solution was collected on a filter. There was thus obtained 1.5 g. of solid which melted at 150°–162° C. It was dissolved in ether and the solution was filtered. By evaporation of the filtrate there was obtained 1.1 g. of off-white solid which melted at 163°–165° C. This product was racemic cis 1,2,3,4,5,6-hexahydro-3-allyl-6-ethyl-11-methyl-8-hydroxy-2,6-methano-3-benzazocine (Formula I: Z = —CH$_2$—CH=CH$_2$; R$^1$ = —C$_2$H$_5$; R$^2$ = —CH$_3$; R$^3$ = —H), having the molecular formula $C_{18}H_{25}NO$.

B. Interaction of racemic cis 1,2,3,4,5,6-hexahydro-3-allyl-6-ethyl-11-methyl-8-hydroxy-2,6-methano-3-benzazocine with acetic anhydride yielded racemic cis 1,2,3,4,5,6-hexahydro-3-allyl-6-ethyl-11-methyl-8-acetoxy-2,6-methano-3-benzazocine (Formula I: Z = —CH$_2$—CH=CH$_2$; R$^1$ = —C$_2$H$_5$; R$^2$ = —CH$_3$; R$^3$ = —CO—CH$_3$), having the molecular formula $C_{20}H_{27}NO_2$, as a thick yellow oil. Treatment of this base with ethereal hydrogen chloride yielded and base hydrochloride, having the molecular formula $C_{20}H_{27}NO_2\cdot HCL$, as an off-white solid, which melted at 200°–210° C.

C. Interaction of racemic cis 1,2,3,4,5,6-hexahydro-3-allyl-6-ethyl-11-methyl-8-hydroxy-2,6-methano-3-benzazocine with nicotinoyl chloride or with a mixed anhydride such as

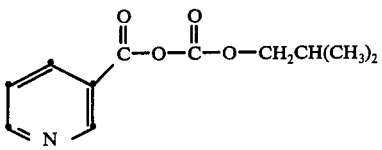

yields racemic cis 1,2,3,4,5,6-hexahydro-3-allyl-6-ethyl-11-methyl-8-nicotinoyloxy-2,6-methano-3-benzazocine (Formula I: Z = —CH$_2$—CH=CH$_2$; R$^1$ = —C$_2$H$_5$; R$^2$ = —CH$_3$; R$^3$ =

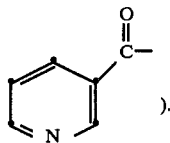

).

D. The following procedure was employed for preparing the racemic cis 1,2,3,4,5,6-hexahydro-6-ethyl-11-methyl-8-hydroxy-2,6-methano-3-benzazocine starting material in the procedure described in part A above.

A solution of 151 g. of p-methoxybenzyl chloride in 925 ml. of anhydrous diethyl ether was added slowly over a period of approximately three hours to a refluxing mixture of 1725 ml. of anhydrous diethyl ether, 50.5 g. of magnesium turnings, and 42.3 g. of magnesium powder. The liquid in the reaction mixture was then siphoned away from the solid, which remained at the bottom of the reaction vessel, into a solution of 127 g. of 3-methyl-4-ethylpyridine methiodide (prepared by interaction of equimolecular amounts of 3-methyl-4-ethylpyridine and methyl iodide) in 925 ml. of diethyl ether. The resulting mixture was stirred for approximately one hour, and the reaction mixture thus obtained was poured into a mixture of ice and water having ½ pound of ammonium chloride dissolved therein. The mixture, which had a lower, aqueous layer and an upper, ethereal layer, was made basic by addition of concentrated ammonium hydroxide. The ethereal layer was then separated from the aqueous layer and dried. The dry ethereal solution was concentrated and the resulting residue, which contained N-methyl-2-(p-methoxybenzyl)-3-methyl-4-ethyl-1,2-dihydropyridine, was dissolved in 430 ml. of methanol. To this solution there was gradually added over a period of fifteen minutes 9.3 g. of sodium borohydride in 80 ml. of ice water, the temperature of the resulting reaction mixture being kept below 20° C. by means of an ice-bath during the addition. The reaction mixture was stirred at room temperature for ½ hour more, and then the methanol was distilled from the reaction mixture, leaving a residue containing N-methyl-2-(p-methoxybenzyl)-3-methyl-4-ethyl-1,2,5,6-tetrahydropyridine.

The foregoing procedure was repeated, using the same amounts of reactants and other materials with the exception that 106 g. of 3-methyl-4-ethylpyridine methiodide was employed instead of 127 g.

The two residues thus obtained containing N-methyl-2-(p-methoxybenzyl)-3-methyl-4-ethyl-1,2,5,6-tetrahydropyridine were combined and the desired product was isolated therefrom as follows. Water and ether were mixed with the combined residues, and the two layers in the resulting mixture were separated, the aqueous layer being discarded, and the ethereal layer was extracted with water to which had been added 80 ml. of concentrated hydrochloric acid. The aqueous extract was made basic by addition of potassium carbonate and was then extracted with diethyl ether. After being dried, the ether extract was fractionally distilled under reduced pressure. The fraction (I) distilling in the range 106° C. at 0.2 mm. pressure to 136° C. at 0.5 mm. pressure weighed 127.1 g. and consisted of almost pure N-methyl-2-(p-methoxybenzyl)-3-methyl-4-ethyl-1,2,5,6-tetrahydropyridine. The fraction (II) distilling at 136°–147° C. at 0.5 mm. pressure weighed 15.9 g.; a substantial proportion of this fraction was an additional yield of N-methyl-2-(p-methoxybenzoyl)-3-methyl-4-ethyl-1,2,5,6-tetrahydropyridine.

A mixture of 127 g. of N-methyl-2-(p-methoxybenzyl)-3-methyl-4-ethyl-1,2,5,6-tetrahydropyridine and 1450 ml. of concentrated (48 per cent) hydrobromic acid was refluxed for approximately 24 hours. The reaction mixture was mixed with decolorizing charcoal and filtered. The filtrate was concentrated and then water was added, which caused separation of an oily layer. Concentrated ammonium hydroxide was added to the mixture, and the solid which formed was collected on a filter. The tan product thus collected weighed 47.8 g. and melted at 231°–246° C. This product consisted largely of racemic cis 1,2,3,4,5,6-hexahydro-3-methyl-6-ethyl-11-methyl-8-hydroxy-2,6-methano-3-benzazocine containing a small amount (about 2 percent) of the corresponding racemic trans form. This solid was suspended in 100 ml. of ethanol, and the suspension was heated, then cooled, and filtered. The pale yellow solid thus collected weighed 37.4 g. and melted at 246°–251° C. This product was substantially pure racemic cis 1,2,3,4,5,6-hexahydro-3-methyl-6-ethyl-11-methyl-8-hydroxy-2,6-methano-3-benzazocine.

A mixture of 40.8 g. of racemic cis 1,2,3,4,5,6-hexahydro-3-methyl-6-ethyl-11-methyl-8-hydroxy-2,6-methano-3-benzazocine and 120 ml. of acetic anhydride was heated on a steam bath for approximately three hours. The reaction mixture was then concentrated, ether was added, and the resulting mixture was added to ice in a separatory funnel. The ethereal layer was collected, washed with a solution of 80 g. of potassium hydroxide in 80 ml. of water, and concentrated under reduced pressure on a steam bath. The syrupy residue thus obtained, which was racemic cis 1,2,3,4,5,6-hexahydro-3-methyl-6-ethyl-11-methyl-8-acetoxy-2,6-methano-3-benzazocine, weighed 44.8 g. This product was dissolved in 125 ml. of chloroform and this solution was added to a solution of 18.6 g. of cyanogen bromide in 90 ml. of chloroform at room temperature. The resulting mixture was refluxed for two and one-half hours. The reaction mixture was then concentrated under reduced pressure to yield a residue which consisted chiefly of racemic cis 1,2,3,4,5,6-hexahydro-3-cyano-6-ethyl-11-methyl-8-acetoxy-2,6-methano-3-benzazocine. To this residue there were added 60 ml. of concentrated hydrochloric acid in 240 ml. of water, and the mixture was refluxed for about 26 hours. The reaction mixture was then concentrated under reduced pressure, diethyl ether and a small volume of water were added, and the mixture was filtered. Some oily material passed through the filter into the filtrate; this was recovered and retained. The solid crystalline product thus collected was dissolved in approximately 200 ml. of hot water, decolorizing charcoal was added and the solution was filtered while hot. Concentrated ammonium hydroxide was added to the solution, which was then cooled. The solid which separated from solution was collected on a filter and dried. A further crop of solid was obtained by working up the oily material mentioned above. The two crops were combined, ground finely, and heated in suspension in 100 ml. of methyl alcohol. The suspension was cooled and filtered. The solid thus collected weighed 16.7 g. and melted at 245°–250° C. with decomposition. This product was racemic cis 1,2,3,4,5,6-hexahydro-6-ethyl-11-methyl-8-hydroxy-2,6-methano-3-benzazocine.

EXAMPLE 2

1,2,3,4,5,6-Hexahydro-3-allyl-6-ethyl-8-hydroxy-2,6-methano-3-benzazocine

Following the procedure described in Example 1 hereinabove but substituting racemic cis 1,2,3,4,5,6-hexahydro-6-ethyl-8-hydroxy-2,6-methano-3-benzazocine in molar equivalent amount for the corresponding 6-ethyl-11-methyl compound used in that example, there is obtained racemic cis 1,2,3,4,5,6-hexahydro-3-allyl-6-ethyl-8-hydroxy-2,6-methano-3-benzazocine (Formula I: Z = —CH$_2$—CH=CH$_2$; R$^1$ = —C$_2$H$_5$; R$^2$ = —H; R$^3$ = —H).

EXAMPLE 3

1,2,3,4,5,6-Hexahydro-3-allyl-11-ethyl-8-hydroxy-2,6-methano-3-benzazocine

Following the procedure described in Example 1 hereinabove but substituting racemic cis 1,2,3,4,5,6-hexahydro-11-ethyl-8-hydroxy-2,6-methano-3-benzazocine in molar equivalent amount for the corresponding 6-ethyl-11-dimethyl compound used in that example, there is obtained racemic cis 1,2,3,4,5,6-hexahydro-3-allyl-11-ethyl-8-hydroxy-2,6-methano-3-benzazocine (Formula I: Z = —CH$_2$—CH=CH$_2$; R$^1$ = —H; R$^2$ = —C$_2$H$_5$; R$^3$ = —H).

EXAMPLE 4

1,2,3,4,5,6-Hexahydro-3-(3-methyl-2-butenyl)-6,11-dimethyl-8-hydroxy-2,6-methano-3-benzazocine A. A mixture of 8.7 g. of racemic cis 1,2,3,4,5,6-hexahydro-6,11-dimethyl-8-hydroxy-2,6-methano-3-benzazocine (which is also known as racemic cis 2'-hydroxy-5,9-dimethyl-6,7-benzomorphan), 6.0 g of 1-bromo-3-methyl-2-butene, 5.0 g. of sodium bicarbonate, and 125 ml. of N,N-dimethylformamide was stirred and refluxed for approximately 4½ hours. The reaction mixture was then filtered, and the solid on the filter was washed with ethanol. The filtrate and the wash liquor were combined, concentrated under reduced pressure, and then extracted with chloroform. The chloroform extract was concentrated under reduced pressure to yield a syrup which weighed 15.8 g. This syrup was dissolved in 120 ml. of diethyl ether and the resulting solution was filtered to remove approximately one-half gram of a brown amorphous solid. The filtrate was extracted with a mixture of 5 ml. of concentrated hydrochloric acid and 20 ml. of water. To the extract there was added 5 ml. of concentrated ammonium hydroxide solution and ice. A pale tan syrup separated from solution and after stirring, this syrup solidified. The resulting pale tan solid was collected and dried; it weighed 10.6 g. After two recrystallizations from a mixture of methyl alcohol and water, with charcoaling, this solid weighed 8.2 g. and melted at 145°–147° C. The product thus obtained was racemic cis 1,2,3,4,5,6-hexahydro-3-(3-methyl-2-butenyl)-6,11-dimethyl-8-hydroxy-2,6-methano-3-benzazocine (Formula II: Y = —CH$_2$—CH=C(CH$_3$)$_2$; R$^3$ = —H), having the molecular formula C$_{19}$H$_{27}$NO. This product was soluble in a mixture of 0.35 ml. of N/2 hydrochloric acid and 0.15 ml. of water to the extent of 10 percent, the pH of the 1 percent solution being 2.80; and when the pH of the 1 percent solution was gradually raised by addition of N/10 sodium hydroxide solution, a precipitate formed at pH 5.4. When the base was converted to the hydrochloride and was then regenerated from this salt it melted at 151°–153° C. The hydrochloride of this base melted at 245°–247° C. (dec.). and the cyclohexylsulfamate of this base melted at 163°–166° C. The base formed a grayish-yellow tannate.

B. Interaction of racemic cis 1,2,3,4,5,6-hexahydro-3-(3-methyl-2-butenyl)-6,11-dimethyl-8-hydroxy-2,6-methano-3-benzazocine with acetic anhydride yields racemic cis 1,2,3,4,5,6-hexahydro-3-(3-methyl-2-butenyl)-6,11-dimethyl-8-acetoxy-2,6-methano-3-benzazocine (Formula II: Y = —CH$_2$—CH=C(CH$_3$)$_2$; R$^3$ = —CO—CH$_3$).

C. Interaction of racemic cis 1,2,3,4,5,6-hexahydro-3-(3-methyl-2-butenyl)-6,11-dimethyl-8-hydroxy-2,6-methano-3-benzazocine with nicotinoyl chloride and with isonicotinoyl chloride, or with an appropriate mixed anhydride, yields respectively, 1,2,3,4,5,6-hexahydro-3-(3-methyl-2-butenyl)-6,11-dimethyl-8-nicotinoyloxy-2,6-methano-3-benzazocine (Formula II: Y = —CH$_2$—CH=C(CH$_3$)$_2$; R$^3$ =

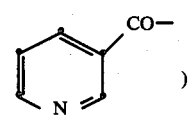
)

and 1,2,3,4,5,6-hexahydro-3-(3-methyl-2-butenyl)-6,11-dimethyl-8-isonicotinoyloxy-2,6-methano-3-benzazocine (Formula II: Y = —CH$_2$—CH=C(CH$_3$)$_2$; R$^3$ =

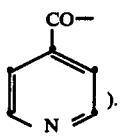

).

D. Following the procedure of part A of this example but using the dextro form in one instance, and the levo form in another instance, of cis 1,2,3,4,5,6-hexahydro-6,11-dimethyl-8-hydroxy-2,6-methano-3-benzazocine (resolved into the dextro and levo forms using d- and l-tartaric acids) instead of the racemic form used in part A, the respective final products were the dextro- and the levo-forms of cis 1,2,3,4,5,6-hexahydro-3-(3-methyl-2-butenyl)-6,11-dimethyl-8-hydroxy-2,6-methano-3-benzazocine. The dextro compound was obtained in the form of an amber colored powder which melted at 179°–182° C. The levo compound was obtained as white crystals which melted at 176°–179° C.

E. Following the procedure of part A of this example, but using as a starting material the racemic form in one instance, the dextro form in another instance, and the levo form in still another instance, of trans 1,2,3,4,5,6-hexahydro-6,11-dimethyl-8-hydroxy-2,6-methano-3-benzazocine instead of the corresponding racemic cis form used in part A, the respective final products were the racemic, dextro, and levo forms of trans 1,2,3,4,5,6-hexahydro-3-(3-methyl-2-butenyl)-6,11-dimethyl-8-hydroxy-2,6-methano-3-benzazocine.

The racemic trans product was converted to its hydrobromide, having the molecular formula C$_{19}$H$_{27}$NO·HBr, which was obtained as white needles which melted at 240°–241° C. (dec.); the solubility of this hydrobromide in water was less than 0.25 percent, and it was soluble in ethanol to the extent of 1 percent (weight/volume), no precipitate being formed on addition of four volumes of water, the pH of the diluted solution being 5.3.

The dextro trans product was converted to its hydrochloride, having the molecular formula C$_{19}$H$_{27}$NO·HCl, which was obtained as white crystals which melted at 254°–255° C. (dec.); this hydrochloride was soluble in water to the extent of 5 percent, the pH of a 1 percent aqueous solution being 5.6, no precipitate being formed when the 1 percent aqueous solution was adjusted to 6.9 by addition of N/10 sodium hydroxide solution.

The levo trans product was converted to its hydrochloride, having the molecular formula C$_{19}$H$_{27}$NO·HCl, which was obtained as white crystals which melted at 254°–255° C. (dec.); this hydrochloride was soluble in water to the extent of 5 percent, the pH of a 1 percent aqueous solution being 5.7, a precipitate being formed when the 1 percent aqueous solution was adjusted to 7.0 by addition of N/10 sodium hydroxide solution.

EXAMPLE 5

1,2,3,4,5,6-Hexahydro-3-(3-hexenyl)-6,11-dimethyl-8-hydroxy-2,6-methano-3-benzazocine Following the procedure described in part A of Example 4 hereinabove but substituting 1-bromo-3-hexene in molar equivalent amount for the 1-bromo-3-methyl-2-butene used in that example, there is obtained racemic cis 1,2,3,4,5,6-hexahydro-3-(3-hexenyl)-6,11-dimethyl-8-hydroxy-2,6-methano-3-benzazocine (Formula II: Y = —CH$_2$CH$_2$—CH=CH—CH$_2$—CH$_3$; R$^3$ = —H).

EXAMPLE 6

1,2,3,4,5,6-Hexahydro-3-(3-hexenyl)-6-ethyl-11-methyl-8-hydroxy-2,6-methano-3-benzazocine Following the procedure described in part A of Example 1 hereinabove but substituting 1-bromo-3-hexene in molar equivalent amount for the allyl bromide used in that example, there is obtained racemic cis 1,2,3,4,5,6-hexahydro-3-(3-hexenyl)-6-ethyl-11-methyl-8-hydroxy-2,6-methano-3-benzazocine (Formula I: Z = —CH$_2$CH$_2$—CH=CH—CH$_2$CH$_3$; R$^1$ = —C$_2$H$_5$; R$^2$ = —CH$_3$; R$^3$ = —H).

EXAMPLE 7

1,2,3,4,5,6-Hexahydro-3-(3-methyl-2-butenyl)-6-ethyl-11-methyl-8-hydroxy-2,6-methano-3-benzazocine A. A mixture of 9.25 g. of racemic cis 1,2,3,4,5,6-hexahydro-6-ethyl-11-methyl-8-hydroxy-2,6-methano-3-benzazocine, 6.0 g. of 1-bromo-3-methyl-2-butene, 125 ml. of N,N-dimethylformamide, and 5.0 g. of sodium bicarbonate was stirred and refluxed for approximately 4½ hours. The reaction mixture was then filtered, and the solid collected on the filter was washed with ethanol. The filtrate and the wash liquor were combined and concentrated under reduced pressure. To the resulting residue there was added 50 ml. of diethyl ether, and the mixture was filtered. Approximately 0.6 g. of solid was collected on the filter, and 8.2 g. of brown solid separated from the filtrate and was collected by filtration. These two crops of solid (8.8 g.) were combined, 25 ml. of methanol was added, and the mixture was boiled. Only a small portion of the solid dissolved. This mixture was mixed with 25 ml. of water and chilled. The mixture was filtered to collect 8.3 g. of pale tan solid which melted at 156°–158° C. The product thus obtained was racemic cis 1,2,3,4,5,6-hexahydro-3-(3-methyl-2-butenyl)-6-ethyl-11-methyl-8-hydroxy-2,6-methano-3-benzazocine (Formula I: Z = —CH$_2$—CH=C(CH$_3$)$_2$; R$^1$ = —C$_2$H$_5$; R$^2$ = —CH$_3$; R$^3$ = —H), having the molecular formula C$_{20}$H$_{29}$NO. The solubility of this product in a mixture of 0.34 ml. of N/2 hydrochloric acid and 19.66 ml. of water was less than 0.25 percent; and its solubility in ethanol was less than 1 percent (weight/volume).

B. Treatment of this base with acetic anhydride yields racemic cis 1,2,3,4,5,6-hexahydro-3-(3-methyl-2-butenyl)-6-ethyl-11-methyl-8-acetoxy-2,6-methano-3-benzazocine (Formula I: Z = —CH$_2$—CH=C(CH$_3$)$_2$; R$^1$ = —C$_2$H$_5$; R$^2$ = —CH$_3$; R$^3$ = —CO—CH$_3$).

C. By interaction of 10.8 g. of racemic cis 1,2,3,4,5,6-hexahydro-3-(3-methyl-2-butenyl)-6-ethyl-11-methyl-8-hydroxy-2,6-methano-3-benzazocine with 11.9 g. of cyclopropanecarbonyl chloride in 125 ml. of pyridine there was obtained 7.0 g. of racemic cis 1,2,3,4,5,6-hexahydro-3-(3-methyl-2-butenyl)-6-ethyl-11-methyl-8-cyclopropanecarbonyloxy-2,6-methano-3-benzazocine hydrochloride, having the molecular formula C$_{22}$H$_{29}$NO$_2$·HCl, which melted at 226°–229° C.

D. Following the procedure of part A of this example but using instead of the racemic cis 1,2,3,4,5,6-hexahydro-6-ethyl-11-methyl-8-hydroxy-2,6-methano-3-benzazocine starting material the corresponding dextro cis, levo cis, racemic trans, dextro trans, and levo trans forms, there were obtained as the respective final products:

dextro cis 1,2,3,4,5,6-hexahydro-(3-methyl-2-butenyl)-6-ethyl-11-methyl-8-hydroxy-2,6-methano-3-benzazocine, which was converted to its hydrochloride salt having the molecular formula $C_{20}H_{29}NO \cdot HCl$, which was obtained as white crystals melting at 219°–221° C. (dec.).

levo cis 1,2,3,4,5,6-hexahydro-(3-methyl-2-butenyl)-6-ethyl-11-methyl-8-hydroxy-2,6-methano-3-benzazocine, which was converted to its hydrochloride salt having the molecular formula $C_{20}H_{29}NO \cdot HCl$ which was obtained as white crystals melting at 219°–220° C. (dec.).

racemic trans 1,2,3,4,5,6-hexahydro-(3-methyl-2-butenyl)-6-ethyl-11-methyl-8-hydroxy-2,6-methano-3-benzazocine, having the molecular formula $C_{20}H_{29}NO$, which was obtained as pale tan crystals melting at 131°–132° C.

dextro trans 1,2,3,4,5,6-hexahydro-(3-methyl-2-butenyl)-6-ethyl-11-methyl-8-hydroxy-2,6-methano-3-benzazocine, which was converted to its hydrochloride salt having the molecular formula $C_{20}H_{29}NO \cdot HCl$, which was obtained as white crystals melting at 237°–238° C.

levo trans 1,2,3,4,5,6-hexahydro-(3-methyl-2-butenyl)-6-ethyl-11-methyl-8-hydroxy-2,6-methano-3-benzazocine, which was converted to its hydrochloride salt having the molecular formula $C_{20}H_{29}NO \cdot HCl$, which was obtained as white crystals melting at 237°–240° C.

EXAMPLE 8

1,2,3,4,5,6-Hexahydro-3-(2-methyl-2-propenyl)-6,11-dimethyl-8-hydroxy-2,6-methano-3-benzazocine Using a procedure similar to that described in part of Example 4 hereinabove, 3.3 g. of 1-chloro-2-methyl-2-propene was interacted with 7.5 g. of racemic cis 1,2,3,4,5,6-hexahydro-6,11-dimethyl-8-hydroxy-2,6-methano-3-benzazocine to produce racemic cis 1,2,3,4,5,6-hexahydro-3-(2-methyl-2-propenyl)-6,11-dimethyl-8-hydroxy-6-methano-3-benzazocine (Formula II: $Y = -CH_2-C(CH_3)=CH_2$; $R^3 = -H$) having the molecular formula $C_{18}H_{25}NO$, which was treated with hydrochloric acid to yield 3.6 g. of the corresponding hydrochloride in the form of off-white crystals which melted at 260°–261° C. (dec.). The solubility of the hydrochloride in water was less than 0.25 percent, and in ethanol was less than 1 percent (weight/volume).

B. Treatment of the base with acetic anhydride yields racemic cis 1,2,3,4,5,6-hexahydro-3-(2-methyl-2-propenyl)-6,11-dimethyl-8-acetoxy-2,6-methano-3-benzazocine.

EXAMPLE 9

1,2,3,4,5,6-Hexahydro-3-(2,3-butadien-1-yl)-6,11-dimethyl-8-hydroxy-2,6-methano-3-benzazocine Using a procedure similar to that described in part A of Example 4 hereinabove, but using 1-bromo-2,3-butadiene ($Br-CH_2-CH=C=CH_2$) in molar equivalent amount in place of the 1-bromo-3-methyl-2-butene used in that example, there is obtained racemic cis 1,2,3,4,5,6-hexahydro-3-(2,3-butadien-1-yl)-6,11-dimethyl-8-hydroxy-2,6-methano-3-benzazocine (Formula II: $Y = -CH_2-CH=C=CH_2$; and $R^3 = -H$).

Compounds of this invention which were prepared as described in the foregoing examples were found to be antagonists of certain strong analgesics. Thus, when tested in rats by a modified D'Amour-Smith test procedure and in dogs, they were found to be antagonists of the analgesic activity of morphine and meperidine. In this test procedure, when the compounds of this invention were administered prior to or simultaneously with administration or morphine or meperidine, the expected analgesic effect of the latter was decreased with increasing dosage levels of the former to a point where no analgesic effect was obtained. And when the new compounds were administered after the administration of morphine or meperidine, the analgesic effect was diminished or terminated, depending on the dosage levels involved. For example representative compounds of this invention, each in the form of an aqueous solution of the lactic acid acid-addition salt, were administered subcutaneously to rats to determine the dosage level, in terms of weight of antogonist per kilogram of body weight of the animal, which caused reduction of the analgesic effect of a 60 mg./kg. dose of meperidine hydrochloride by approximately 50 per cent or 15 mg./kg. dose of morphine sulfate, so that the analgesic effect produced by the combination of the antagonist and the meperidine hydrochloride or the morphine sulfate was substantially the same as the analgesic effect produced by a 30 mg./kg. dose of meperidine hydrochloride alone or 7.5 mg./kg. of morphine sulfate alone, respectively. The results thus obtained for the lactic acid acid-addition salt of each of the indicated compounds were as follows:

| Compound of Example No. | mg./kg. versus meperidine | mg./kg. versus morphine |
|---|---|---|
| 1A | 0.049 | 0.044 |
| 1B | 0.027 | |
| 4A (base) | 3.9 | 9.0 |
| 4A (cyclohexyl-sulfamate) | [125;orally] | |
| 4D (dextro) | 18.0 | 21.0 |
| 4D (levo) | 1.05 | 4.3 |
| 4E (racemic) | 3.3 | |
| 4E (dextro) | 13.0 | |
| 4E (levo) | 0.55 | |
| 7A | 10.9 | 11.6 |
| 7C | 0.0022 | |
| 7D (dextro cis) | 19.5 | |
| 7D (levo cis) | 3.1 | |
| 8A | 0.094 | 0.19 |

When tested as analgesics by conventional methods in mice and rats, the compounds of Formulas I and II, with the exception of the trans compounds of Example 7D as noted below, gave negative results.

In tests as in animals as analgesics and as antagonists of strong analgesics, the racemic, dextro, and levo forms of trans 1,2,3,4,5,6-hexahydro-3-(3-methyl-2-butenyl)-6-ethyl-11-methyl-8-hydroxy-2,6-methano-3-benzazocine described in Example 7D above gave results substantially differing from those of the corresponding cis forms and of the related compounds of this invention. Thus, in the analgesic antagonist test versus a 60 mg/kg. dose of meperidine, the maximum degree of antagonism which could be obtained for these three trans forms was: for the racemic trans form, 50 percent antagonism at 0.1 mg/kg.; for the dextro trans form, 30 percent antagonism at 1.25 mg./kg.; and for the levo trans form, 22 percent antagonism at 0.1 mg./kg. Moreover, the racemic trans and levo trans forms gave positive results in the D'Amour-Smith test for analgesia in rats, viz., $ED_{50}$ values of 1.4 mg./kg. and 0.94 mg./kg., respectively. In this test, the dextro trans form was inactive at 30 mg./kg., and was toxic at 60 mg./kg.

In human subjects, however, the compounds of Formulas I and II are valuable and effective agents for producing analgesia when administered in the general range of about 10 to 500 mg. per 70 kg. of subject weight, the dosage depending of course on the particular compound, the mode of administration, and the like. The following clinical results which were obtained in human subjects are illustrative. For oral administration the free base was used, and for parenteral (usually intramuscular) administration an aqueous solution of the lactate salt was used; the dosages are expressed in each instance in terms of milligrams of base per 70 kilograms of body weight of the human subject.

As an analgesic agent in humans, 1,2,3,4,5,6-hexahydro-3-allyl-6-ethyl-11-methyl-8-hydroxy-2,6-methano-3-benzazocine, obtained as described in Example 1A above, is used orally at a dosage in the approximate range 5–50 mg./70 kg. and is used parenterally at a dosage in the approximate range 2–10 mg./70 kg. For example, when this compound of Example 1A was administered to human subjects parenterally at doses of 5 mg./kg. and 10 mg./kg., effective and satisfactory analgesia was produced in the subjects. Parenterally in humans, 5 mg. of the compound of Example 1A is approximately equivalent to 10 mg. of morphine sulfate as an analgesic.

As an analgesic agent in humans, 1,2,3,4,5,6-hexahydro-3-(3-methyl-2-butenyl)-6,11-dimethyl-8-hydroxy-2,6-methano-3-benzazocine, obtained as described in Example 4A above, is used orally at a dosage in the approximate range 10–500 mg./70 kg. and is used parenterally at a dosage in the approximate range 10–350 mg./70 kg. For example, when this compound of Example 4A was administered to human subjects orally at doses of 50mg./70 kg. and 100 mg./70 kg., and parenterally at 10 mg./70 kg. and 60 mg./70 kg., effective and satisfactory analgesia was produced in the subjects. Results in stabilized morphine addicts indicated that this compound did not support morphine addiction in these addicts. Parenterally in humans, 20 mg. of the compound of Example 4A is approximately equivalent to 10 mg. of morphine sulfate as an analgesic.

As an analgesic agent in humans, 1,2,3,4,5,6-hexahydro-3-(3-methyl-2-butenyl)-6-ethyl-11-methyl-8-hydroxy-2,6-methano-3-benzazocine, obtained as described in Example 7A above, is used orally at a dosage in the approximate range 25–500 mg./70 kg. and is used parenterally at a dosage in the approximate range 10–100 mg./70 kg. For example, when this compound of Example 7A was administered to human subjects parenterally at doses of 10 mg./70 kg. to 80 mg./70 kg., effective and satisfactory analgesia was produced in the subjects. Parenterally in humans, 40 mg. of the compound of Example 7A is approximately equivalent to 10 mg. of morphine sulfate as an analgesic.

I claim:
1. 1,2,3,4,5,6-Hexahydro-3-(3-methyl-2-butenyl)-6,11-dimethyl-8-hydroxy-2,6-methano-3-benzazocine having the structural formula

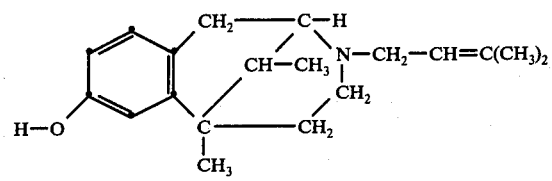

2. 1,2,3,4,5,6-Hexahydro-3-(2,3-butadien-1-yl)-6,11-dimethyl-8-hydroxy-2,6-methano-3-benzazocine having the structural formula

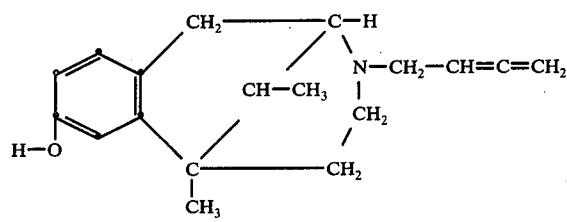

3. cis 1,2,3,4,5,6-Hexahydro-3-(3-methyl-2-butenyl)-6,11-dimethyl-8-hydroxy-2,6-methano-3-benzazocine.

4. dextro cis 1,2,3,4,5,6-Hexahydro-3-(3-methyl-2-butenyl)-6,11-dimethyl-8-hydroxy-2,6-methano-3-benzazocine.

5. levo cis 1,2,3,4,5,6-Hexahydro-3-(3-methyl-2-butenyl)-6,11-dimethyl-8-hydroxy-2,6-methano-3-benzazocine.

6. A nontoxic acid addition salt of 2-$\beta,\beta$-dimethylallyl-5,9-dimethyl-2'-hydroxy-6,7-benzmorphan.

7. 2-$\beta,\beta$-Dimethylallyl-5,9-dimethyl-2'-hydroxy-6,7-benzmorphan hydrochloride.

8. Iso-2-$\beta,\beta$-dimethylallyl-5,9-dimethyl-2'-hydroxy-6,7-benzmorphan.

9. A chemical compound of the class consisting of a free base and its nontoxic, acid addition salts, the free base having the formula:

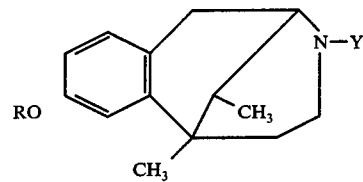

in which R is a member selected from the group consisting of hydrogen, and acetyl, and Y is a polymethylallyl group having 5 to 6 carbon atoms.

* * * * *

UNITED STATES PATENT AND TRADEMARK OFFICE
CERTIFICATE OF CORRECTION

PATENT NO. : 4,105,659
DATED : August 8, 1978
INVENTOR(S) : Sydney Archer

It is certified that error appears in the above-identified patent and that said Letters Patent is hereby corrected as shown below:

Column 1, line 20, "($R^3$-O-)2,6-methano-" should read -- ($R^3$-O-)-2,6-methano- --.

Column 2, line 28, "benzozocines" should read -- benzazocines --.

Column 3, line 11, "benzozocine" should read -- benzazocine --.

Column 4, line 53, "phoshonic" should read -- phosphonic --.

Column 5, line 58, "optionally" should read -- optically --.

Signed and Sealed this

Eleventh Day of February 1986

[SEAL]

Attest:

DONALD J. QUIGG

Attesting Officer     Commissioner of Patents and Trademarks